United States Patent [19]

Giannella

[11] Patent Number: 5,575,646
[45] Date of Patent: Nov. 19, 1996

[54] SUPPORT DEVICE FOR A DENTIST'S DRILL

[75] Inventor: Gianni M. Giannella, Via Frejus, 54 I-10139 Torino, Italy

[73] Assignees: Gianni M. Giannella; Francesco Giannella, both of Italy

[21] Appl. No.: 347,319

[22] PCT Filed: Jun. 2, 1993

[86] PCT No.: PCT/EP93/01388

§ 371 Date: Jan. 12, 1995

§ 102(e) Date: Jan. 12, 1995

[87] PCT Pub. No.: WO93/24069

PCT Pub. Date: Dec. 9, 1993

[30] Foreign Application Priority Data

Jun. 3, 1992 [IT] Italy ................... TO92A0474

[51] Int. Cl.⁶ ............................................ A61C 3/02
[52] U.S. Cl. ............................................ 433/76; 433/77
[58] Field of Search ............................ 433/75, 76, 77, 433/78, 79, 108, 109, 107

[56] References Cited

U.S. PATENT DOCUMENTS

| 153,943 | 8/1874 | Gray | 433/79 X |
|---|---|---|---|
| 354,976 | 12/1886 | Field | 433/79 X |
| 500,139 | 6/1893 | Delking | 433/107 |
| 1,054,028 | 2/1913 | Pieper | 433/107 |
| 2,801,469 | 8/1957 | Solle . | |
| 3,073,561 | 1/1963 | Jermyn | 433/76 X |
| 3,083,462 | 4/1963 | Jermyn . | |
| 3,386,766 | 6/1968 | Gorelick . | |
| 5,281,136 | 1/1994 | Giannella et al. | 433/76 |
| 5,332,391 | 7/1994 | Jermyn | 433/76 |

FOREIGN PATENT DOCUMENTS 2166240  8/1973  France .

*Primary Examiner*—Nicholas D. Lucchesi
*Attorney, Agent, or Firm*—Edward D. Manzo; Mark J. Murphy; Ted K. Ringsred

[57] ABSTRACT

A support device for a dentist's drill comprising a support, an articulated arm comprising two articulated quadrilateral devices disposed in series with one another, and an adjustment device operable to vary the direction of the working axis of the drill. The support is provided with a fixing device for connecting it to a seat back of a dentist's chair and the articulated arm can assume a working condition in which the two articulated quadrilateral devices are disposed at 90° to one another.

7 Claims, 4 Drawing Sheets

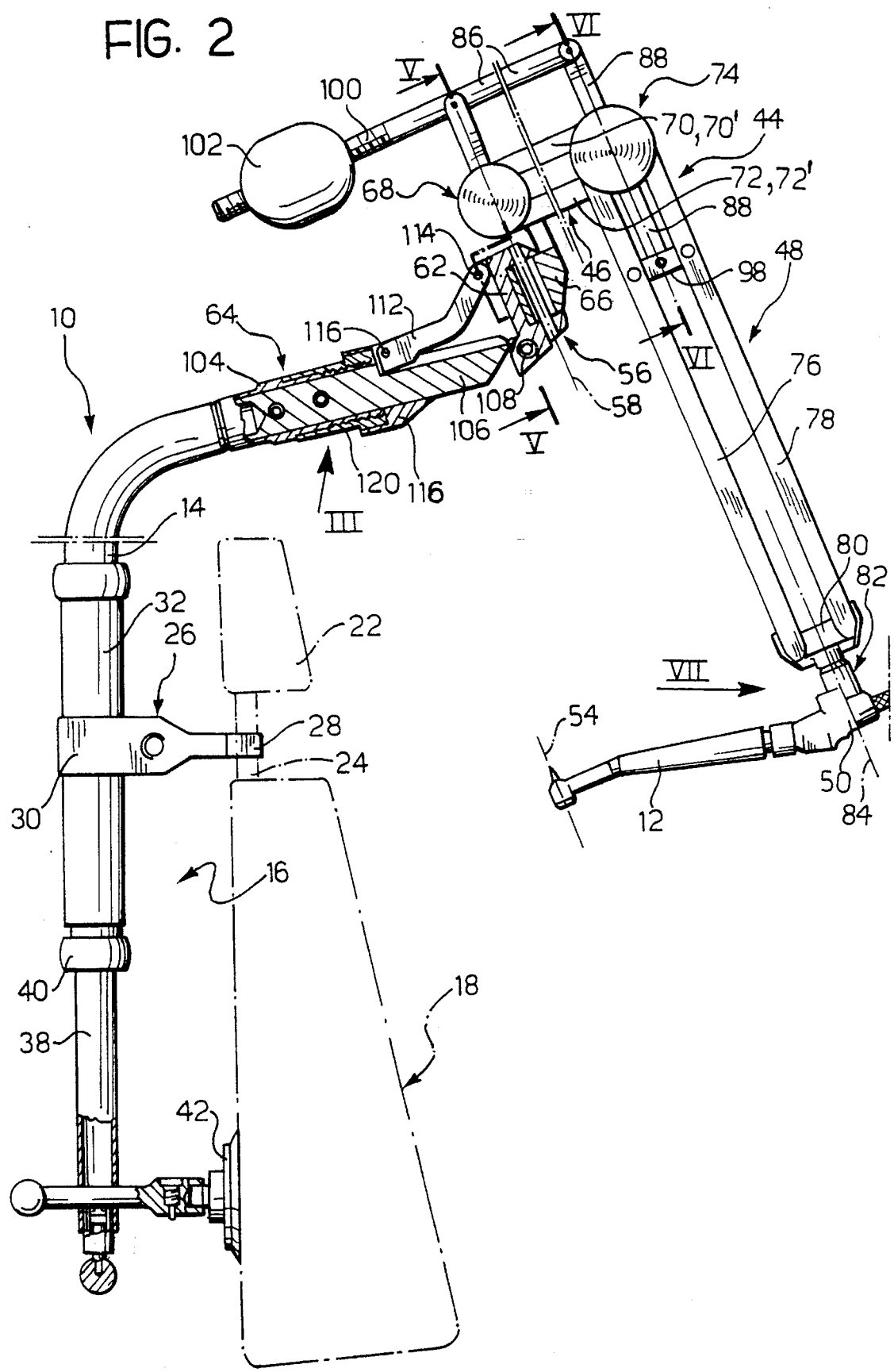

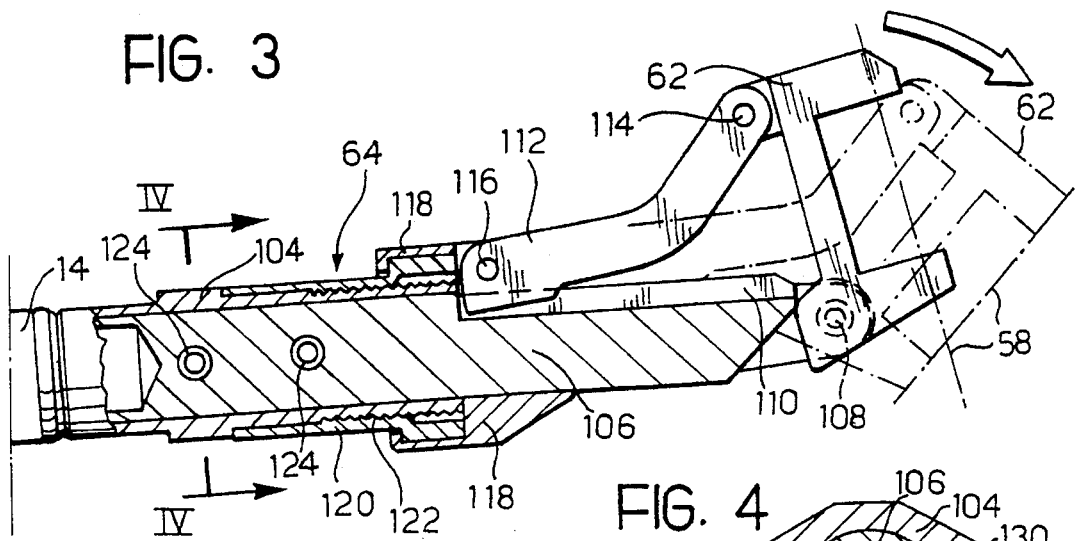
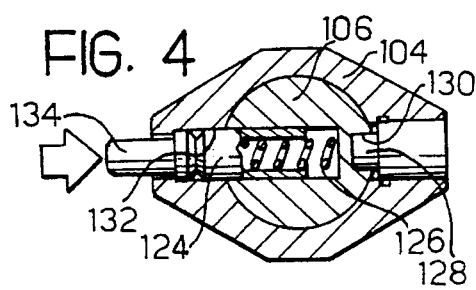
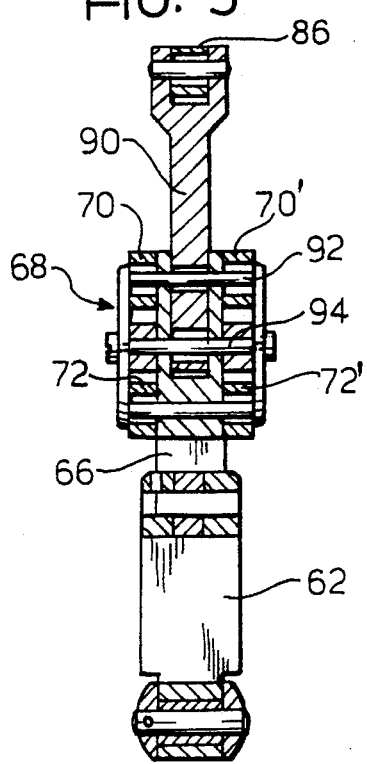
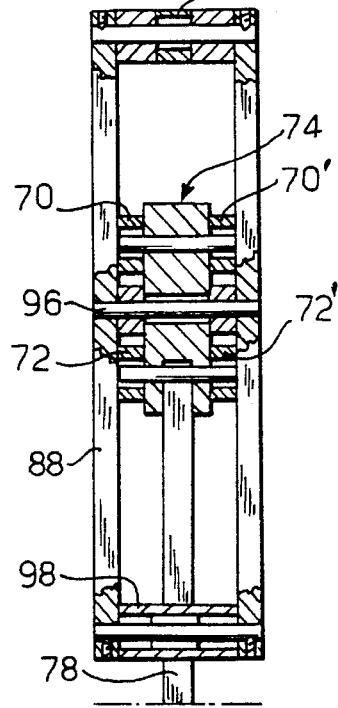

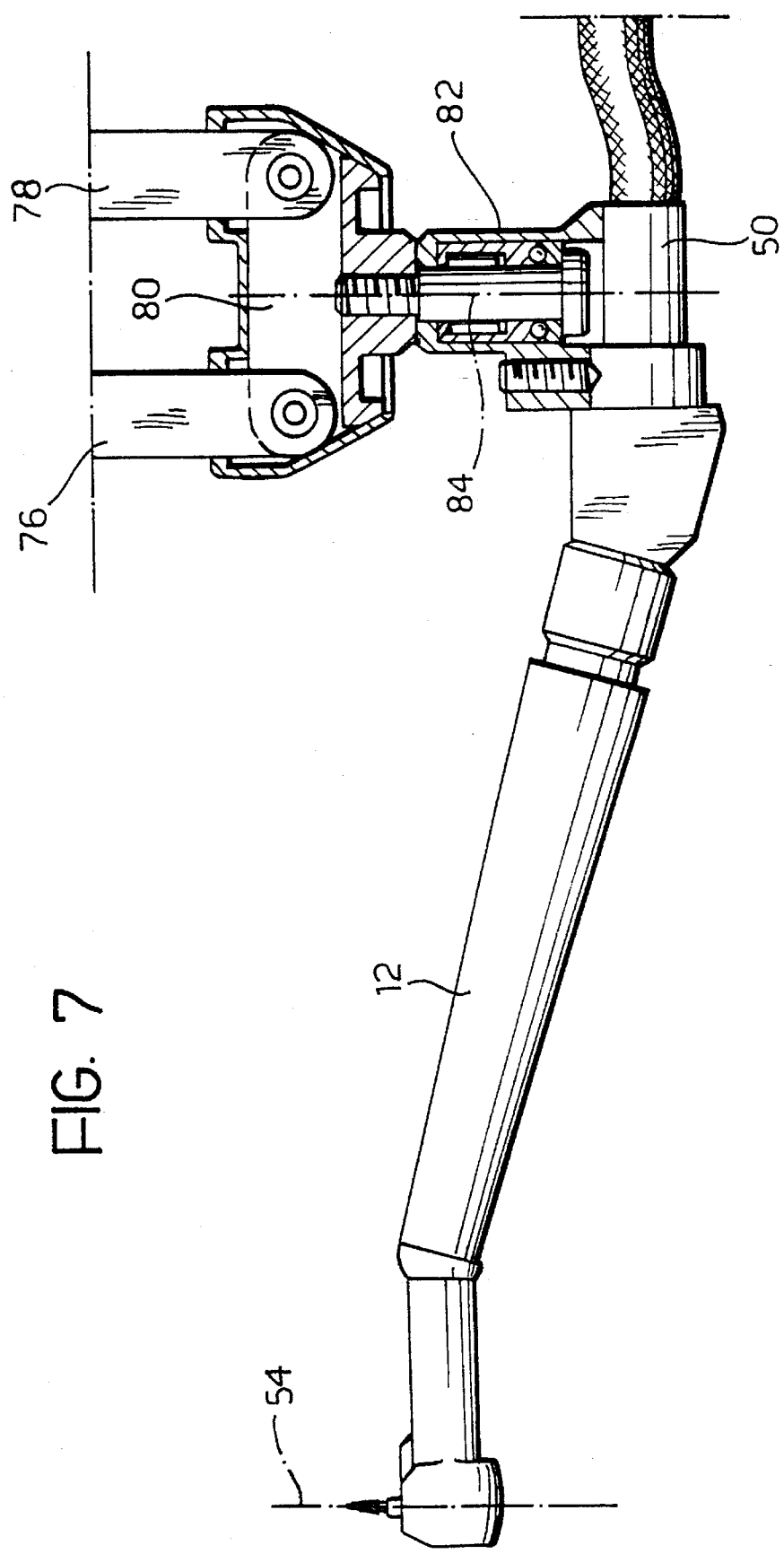

5,575,646

SUPPORT DEVICE FOR A DENTIST'S DRILL

BACKGROUND OF THE INVENTION

The present invention relates to a support device for a dentist's drill.

Tooth drilling or milling operations are normally performed by guiding the drill freehand. This technique is imprecise and leaves room for errors which become critical if the milling of the teeth is performed as part of the preparation for a prosthesis, which consists of milling the tooth (or teeth) in such a way as to cut them down to the shape of a conical stump over which the dental prosthesis is fitted. In this type of operation it is essential that high precision be guaranteed in forming the conical walls of the teeth.

Support devices for dentist's drills have previously been proposed which make it possible to set the working axis of the drill in a predetermined direction and maintain the working axis constantly parallel to itself during use.

Examples of such devices are contained in documents U.S. Pat. No. 3,083,462, U.S. Pat. No. 2,801,469 and FR-A-2 166 240.

From the German document DE-A-3 500 921 there is known a device having an articulated arm with two articulated quadrilateral devices disposed in series with one another, connected to a fixed support base by means of a hinged joint and carrying attachment means for a dentist's drill.

SUMMARY OF INVENTION

The object of the present invention is to provide a simple and compact support device which does not obstruct the working region in front of the patient and which can be easily installed in any already existing dental surgery.

According to the invention this object is achieved by a device having the characteristics of a support; an articulated arm having two articulated quadrilateral devices disposed in series with one another, one of said articulated quadrilateral devices being connected to said support while another of said articulated quadrilateral devices carries a means for attachment of the dental drill in such a way that a working axis of the drill can be located within the working region of the patient whilst remaining constantly parallel to itself; and an adjustment means operable to vary the direction of the working axis of the drill and located between said support and said articulated arm, wherein said support is provided with a fixing means for connecting it to a seat back of a chair and wherein said articulated arm is able to assume a working configuration in which said two articulated quadrilateral devices are located 90° to one another, with said one articulated quadrilateral device being situated above the head of the patient and said another articulated quadrilateral device being disposed substantially in front of the patient.

BRIEF DESCRIPTION OF THE DRAWINGS

Further characteristics and advantages of the invention will become apparent during the course of the following detailed description, given purely by way of nonlimitative example, with reference to the attached drawings, in which:

FIG. 2 is a side view in the direction of the arrow II of FIG. 1;

FIG. 3 is a section illustrating the detail indicated by the arrow III in FIG. 2;

FIG. 4 is a section taken on the line IV—IV of FIG. 3;

FIGS. 5 and 6 are sections taken on the lines V—V and VI—VI of FIG. 2; and

FIG. 7 is a view on an enlarged scale of the part indicated by the arrow VII of FIG. 2.

DETAILED DESCRIPTION OF THE PRESENTLY PREFERRED EMBODIMENT

Figure 1:
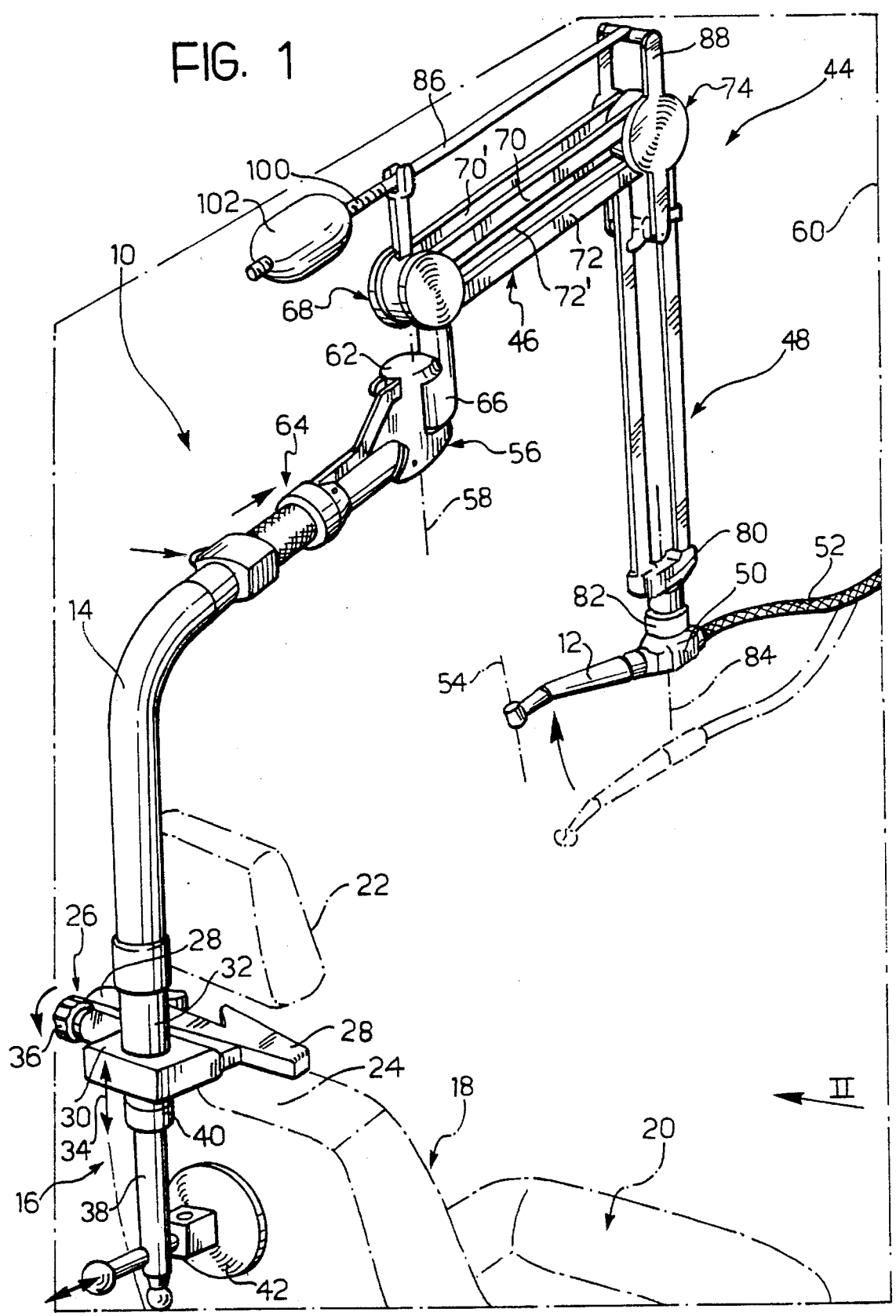
FIG. 1 is a perspective view of a device according to the present invention fitted to a dentist's chair.

With reference to FIGS. 1 and 2, a device for supporting and guiding a dentist's drill 12 is generally indicated with the reference numeral 10.

The device 10 comprises a support base having a generally L-shaped tubular column 14. The column 14 is provided with a fixing device generally indicated 16, by means of which the device 10 can be connected to the seat back 18 of a dentist's chair 20. The dentist's chair 20 is provided, in a manner known per se, with a height-adjustable head rest 22 carried by a metal bar 24 projecting from the upper part of the seat back 18.

The fixing device 16 comprises a clamp 26 having two movable jaws 28 which grip the metal bar 24 of the head rest 22 by the clamping effect of a screw not illustrated in the drawings.

The clamp 26 has a base 30 with a hole through which a cylindrical section 32 of the column 14 is slidable. The position of the column 14 with respect to the clamp 26 can be adjusted by means of the movement indicated by the double arrow 34 in FIG. 1. A screw 36 allows clamping of the base 30 onto the cylindrical section 32 of the column 14, thereby preventing relative movement between these two. From the lower end of the column 14 projects a telescopic element 38 which is fixed to the column 14 by a clamping ring nut 40. The telescopic element 38 carries a suction pad 42 which lies against the rear surface of the seat back 18.

The column 14 carries an articulated arm 44 two articulated quadrilateral devices 46, 48 disposed in series with one another. The articulated arm 44 carries at its free end an attachment member 50 on which a dentist drill 12 of conventional type can be engaged, such drill being provided with its own flexible supply duct 52 for supplying compressed air, water and possibly electrical energy to the drill 12.

The two articulated quadrilateral devices 46, 48 are disposed in such a way that in the configuration in which their internal angles are all equal to 90° (the configuration in which the tip of the drill 12 is located at the centre of the working region) the two devices 46, 48 are situated 90° from one another with the first articulated quadrilateral device 46 extending above the head of the patient and the second articulated quadrilateral device 48 being situated largely in front of the patient.

In FIGS. 1 and 2 the working axis of the drill 12 is indicated 54. The two articulated quadrilateral devices 46, 48 allow any displacement of the tip of the drill to be effected within the working area, maintaining the working axis 54 constantly parallel to a pre-set direction orthogonal to the occlusal plane of the patient.

The articulated arm 44 is connected to the support base 14 by means of a pivotal coupling 56 having a pivot axis 58 parallel to the working axis 54 of the drill 12. The pivotal coupling 56 allows the articulated arm 44 to be displaced to one side or the other of a vertical mid plane 60 (FIG. 1). The pivotal coupling 56 includes a first part 62 which is connected to the support base 14 by means of an adjustment device 64 which will be described in detail hereinbelow. A second part 66 of the pivotal coupling 56 carries a support 68 to which are articulated two pairs of rods 70, 72 and 70', 72' forming part of the first articulated quadrilateral device 46 (see FIGS. 1 and 5).

The two pairs of rods 70, 72 and 70', 72' are pivotally connected to an intermediate support 74 (FIGS. 2 and 6) to which two rods 76, 78 forming part of the second articulated quadrilateral device 48 are also pivotally connected.

With reference to FIG. 7, the rods 76, 78 of the second articulated quadrilateral device 48 are in turn pivotally connected to a terminal support 80 to which is connected the attachment member 50 of the drill 12 with the interposition of a pivotal coupling 82 the axis 84 of which lies parallel to the working axis 54 of the drill 12.

With reference to FIGS. 1 and 2, the two articulated quadrilateral devices 46, 48 are associated with a counterbalancing device which includes a rod 86 constrained to move parallel to the rods of the first articulated quadrilateral device 46. The rod 86 is pivotally connected to a pivotal connection member 88 which is constrained to move parallel to the rods 76, 78 of the second articulated quadrilateral device 48. With reference to FIG. 5, the rod 86 is connected to the support 68 by means of a member 90 which engages a pair of pins 92, 94. With reference to FIGS. 2 and 6, the pivotal connection member 88 is pivotally connected to the intermediate support 74 by means of a pin 96 and is further pivotally connected to the two rods 76, 78 of the second articulated quadrilateral device 48 by means of an element 98. The rod 86 of the counterbalancing device has a threaded section 100 on which is mounted a balancing mass 102 which can be displaced along the axis of the rod 86 to effect an adjustment of the counterbalancing action on the weight of the articulated arm 44 and the parts connected to it.

With reference to FIGS. 2 and 3, the articulated arm 44 is connected to the support base 14 by means of a device 64 which allows adjustment of the inclination of the working axis 54 of the drill 12. The device 64 comprises a sleeve 104 which is slidably mounted on an end section 106 of the support 14. The end section 106 carries a pin 108 on which is pivoted the first part 62 of the pivotal connection 56. The end section 106 has a longitudinal groove 110 within which is fitted a link 112 having a first end pivoted at 114 to the first part 62 of the pivotal connection 56 and a second end pivotally connected at 116 to a member 118 which is axially constrained but is free to rotate with respect to a screw adjustment element 120 which engages a threaded section 122 of the sleeve 104.

With reference to FIGS. 3 and 4, the end part 106 of the support base 14 carries a pair of pins 124 urged radially outwardly by respective coil springs 126.

With reference to FIG. 4, the sleeve 104 is free to slide on the end part 106, but is constrained against rotation with respect to this latter by means of a peg 128 which engages an axial groove 130 in the end part 106. The sleeve 104 is provided with a radial hole 132 in which a push button 134 is slidable.

The adjustment device 64 makes it possible to obtain a large snap adjustment movement, obtained by sliding the sleeve 104 between two operative positions. To pass from one to the other of these operative positions it is sufficient to press the push button 134 in such a way as to disengage the pin 124 from the hole 132 and displace the sleeve 104 until the other pin 124 engages the hole 132 of the sleeve 104.

The device 64 further allows a fine adjustment to be effected in addition to the said snap adjustment, by means of a rotation of the threaded element 120 which makes it possible to obtain a micrometric displacement of the member 118 with respect to the sleeve 104.

The snap adjustment movement makes it possible to move rapidly from operating conditions adapted to work on the upper dental arch to operating conditions necessary to work on the lower dental arch. In addition to variation in the inclination of the working axis 54 it is also necessary to rotate the drill 12 through 180° with respect to the attachment member 50. The attachment member 50 also allows rotation of the drill through different angles to allow rounding, smoothing and bevelling operations to be performed.

After having set the direction of the working axis 54 by means of the adjustment device 64 and possibly by means of a rotation of the drill 12 with respect to the attachment member 50, the tip of the drill can be displaced to all points within the area, always remaining constantly parallel to itself.

The weight of the articulated arm 44 and of the drill 12 is exactly compensated by the counterweight device, so that during the working operation the drill 12 remains virtually weightless and does not strain the dentist's hand.

The two pivotal couplings 56 and 82 disposed at both ends of the articulated arm 44 make it possible to reach working zones situated away from the mid plane 60 and further permit the articulated arm 44 to be displaced to one side or the other of this plane so that the articulated arm 44 does not obstruct the region in front of the patient's mouth.

An important characteristic of the device according to the invention is the fact that the device is fixed to the seat back 18 of the dentist's chair 20 and is movable with the latter so that variations in inclination of the seat back 18 do not modify the existing relationship between the working axis 54 and the patient's mouth. The device is moreover adaptable to any existing dentist's chair without it being necessary to introduce modifications thereto.

I claim:

1. A support device for a dental drill for use in a working region of a dental patient comprising:

a support;

an articulated arm having two articulated quadrilateral devices disposed in series with one another, one of said articulated quadrilateral devices being connected to said support while another of said articulated quadrilateral devices carries a means for attachment of the dental drill in such a way that a working axis having a set angular position of the drill can be located within the working region of the patient whilst remaining constantly parallel to the set angular position; and an adjustment means operable to vary the direction of the working axis of the drill and located between said support and said articulated arm, wherein said support is provided with a fixing means for connecting it to a seat back of a chair and wherein said articulated arm is able to assume a working configuration in which said two articulated quadrilateral devices are located 90° to one another, with said one articulated quadrilateral device being situated above the head of the patient and said another articulated quadrilateral device being disposed substantially in front of the patient.

2. A device according to claim 1 further comprising a counterbalancing device operable to balance the weight of said articulated arm and all devices connected there to.

3. A device according to claim 2, wherein said counterbalancing device includes two pivotal coupling articulation members pivotally coupled together and constrained to move parallel with respective to said articulated quadrilateral devices, and wherein one of said pivotal coupling members has a counterbalancing mass which is adjustably movable along an axis of said one member.

4. A device according to claim 1, wherein said means for adjusting the direction of the working axis of the drill comprises a snap adjustment device for effecting a movement of large magnitude and a micro metric adjustment device for effecting a fine adjustment.

5. A device according to claim 1 further comprising a first pivotal coupling having an axis parallel to the working axis of the drill, and located between the articulated arm and the support.

6. A device according to claim 5 further comprising a second pivotal coupling having an axis parallel to the working axis of the drill, and located between said another articulated quadrilateral device and said attachment means for the drill.

7. A device according to claim 1, wherein said fixing means for the support comprise a clamp operable to grip a bar supporting a headrest of the chair and a contact pad acting against the rear surface of the seat back.

* * * * *